(12) United States Patent
Yotsuhashi et al.

(10) Patent No.: US 8,696,883 B2
(45) Date of Patent: *Apr. 15, 2014

(54) METHOD FOR REDUCING CARBON DIOXIDE

(71) Applicant: Panasonic Corporation, Osaka (JP)

(72) Inventors: Satoshi Yotsuhashi, Osaka (JP); Masahiro Deguchi, Osaka (JP); Yuka Yamada, Nara (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,809

(22) Filed: Nov. 12, 2012

(65) Prior Publication Data

US 2013/0062216 A1 Mar. 14, 2013

Related U.S. Application Data

(63) Continuation of application No. PCT/JP2011/004728, filed on Aug. 25, 2011.

(30) Foreign Application Priority Data

Oct. 6, 2010 (JP) .................................. 2010-226338
Feb. 21, 2011 (JP) .................................. 2011-034087
Apr. 22, 2011 (WO) .................. PCT/JP2011/002391

(51) Int. Cl.
*C25B 3/04* (2006.01)
*C25B 1/00* (2006.01)

(52) U.S. Cl.
CPC .. *C25B 1/003* (2013.01); *C25B 3/04* (2013.01)
USPC .......................................................... 205/340

(58) Field of Classification Search
CPC .................................. C25B 1/003; C25B 3/04
USPC .......................................................... 205/340
See application file for complete search history.

(56) References Cited

U.S. PATENT DOCUMENTS 3,649,485 A * 3/1972 Chisholm ...................... 205/504
4,219,392 A * 8/1980 Halmann ....................... 205/340

(Continued)

FOREIGN PATENT DOCUMENTS

EP 0866506 A1 9/1998
JP 50-115178 A 9/1975

(Continued)

OTHER PUBLICATIONS

Zafrir et al, "Photoelectrochemical reduction of carbon dioxide to formic acid, formaldehyde, and methanol on p-gallium arsenide in aqueous V(II)-V(III) chloride redox system," J. Electroanal. Chem. v. 159 (1983), pp. 373-389.*
Hori et al., "Production of CO and CH4 in Electrochemical Reduction of CO2 at Metal Electrodes in Aqueous Hydrogencarbonate Solution". Chemistry Letters, pp. 1695-1698 (1985).

(Continued)

*Primary Examiner* — Keith Hendricks
*Assistant Examiner* — Colleen M Raphael
(74) *Attorney, Agent, or Firm* — McDermott Will & Emery LLP

(57) ABSTRACT

The present subject matter provides a method for reducing carbon dioxide with the use of a device for reducing carbon dioxide. The device includes a cathode chamber, an anode chamber and a solid electrolyte membrane. The cathode chamber includes a working electrode which includes a metal or a metal compound. The anode chamber includes a counter electrode which includes a region formed of a nitride semiconductor. First and second electrolytic solutions are held in the cathode and anode chamber, respectively. The working electrode and the counter electrode are in contact with the first and second electrolytic solution, respectively. The solid electrolyte membrane is interposed between the cathode and anode chambers. The first electrolyte solution contains the carbon dioxide. An electric source is not interposed electrically between the working electrode and the counter electrode.

23 Claims, 6 Drawing Sheets

(56) References Cited

U.S. PATENT DOCUMENTS

| | | | | |
|---|---|---|---|---|
| 4,240,882 A | * | 12/1980 | Ang et al. | 205/340 |
| 4,381,978 A | * | 5/1983 | Gratzel et al. | 205/340 |
| 4,414,080 A | * | 11/1983 | Williams et al. | 205/340 |
| 4,523,981 A | * | 6/1985 | Ang et al. | 205/340 |
| 4,545,872 A | * | 10/1985 | Sammells et al. | 205/340 |
| 4,668,349 A | * | 5/1987 | Cuellar et al. | 205/555 |
| 4,975,161 A | * | 12/1990 | Nidola et al. | 205/532 |
| 5,022,970 A | * | 6/1991 | Cook et al. | 205/340 |
| 6,204,545 B1 | * | 3/2001 | Nakata | 136/250 |
| 7,750,234 B2 | * | 7/2010 | Deng et al. | 136/258 |
| 8,138,380 B2 | * | 3/2012 | Olah et al. | 205/450 |
| 8,313,634 B2 | * | 11/2012 | Bocarsly et al. | 205/440 |
| 8,414,758 B2 | * | 4/2013 | Deguchi et al. | 205/340 |
| 2008/0245672 A1 | * | 10/2008 | Little et al. | 205/555 |
| 2009/0045072 A1 | * | 2/2009 | Fujii et al. | 205/340 |
| 2011/0203661 A1 | * | 8/2011 | Taniguchi et al. | 136/258 |
| 2013/0118907 A1 | * | 5/2013 | Deguchi et al. | 205/340 |
| 2013/0126359 A1 | * | 5/2013 | Deguchi et al. | 205/340 |

FOREIGN PATENT DOCUMENTS

| | | |
|---|---|---|
| JP | 55-105625 A | 8/1980 |
| JP | 01-313313 A | 12/1989 |
| JP | 05-059562 A | 3/1993 |
| JP | 05-311476 A | 11/1993 |
| JP | 06-158374 A | 6/1994 |
| JP | 07-188961 A | 7/1995 |
| JP | 2000-254508 A | 9/2000 |
| JP | 2003-024764 A | 1/2003 |
| JP | 2003-275599 A | 9/2003 |
| JP | 2004-059507 A | 2/2004 |
| JP | 2007-107043 A | 4/2007 |
| JP | 2009-125609 A | 6/2009 |
| WO | WO-98/15983 A1 | 4/1998 |

OTHER PUBLICATIONS

International Search Report mailed Sep. 27, 2011 issued in corresponding International Application No. PCT/JP2011/004728.

* cited by examiner

METHOD FOR REDUCING CARBON DIOXIDE

This is a continuation of International Application No. PCT/JP2011/004728, with an international filing date of Aug. 25, 2011, which claims priorities of Japanese Patent Application No. 2010-226338, filed on Oct. 6, 2010, Japanese Patent Application No. 2011-034087, filed on Feb. 21, 2011, and International Application No. PCT/JP2011/002391, filed on Apr. 22, 2011, the contents of each of which are hereby incorporated by reference.

The present disclosure relates to a method for reducing carbon dioxide.

Patent Literatures 1-2 disclose a method for reducing carbon dioxide by using an anode electrode formed of n-type photosemiconductor material such as $TiO_2$.

Patent Literatures 3-4 disclose a method for electrolyzing water.

CITATION LIST

Patent Literature

[Patent Literature 1]
Japanese Laid-Open Patent Application Publication No. Hei 07-188961
[Patent Literature 2]
Japanese Laid-Open Patent Application Publication No. Hei 05-311476
[Patent Literature 3]
Japanese Laid-Open Patent Application Publication No. Sho 50-115178
[Patent Literature 4]
Japanese Laid-Open Patent Application Publication No. Hei 2003-024764

SUMMARY

Technical Problem

The methods disclosed in Patent Literatures 1-2 require an electric source between the anode electrode and a cathode electrode to reduce carbon dioxide. The present disclosure provides a novel method for reducing carbon dioxide without such an electric source.

Solution to Problem

The present disclosure relates to a method for reducing carbon dioxide with the use of a device for reducing carbon dioxide. The method includes the following steps. A step (a) is a step of preparing the device for reducing carbon dioxide. The device for reducing carbon dioxide includes a cathode chamber, an anode chamber and a solid electrolyte membrane. The cathode chamber includes a working electrode, and the working electrode includes a metal or a metal compound. The anode chamber includes a counter electrode and the counter electrode includes a region formed of a nitride semiconductor on the surface thereof. In the device, a first electrolytic solution is held in the cathode chamber, and a second electrolytic solution is held in the anode chamber. The working electrode is in contact with the first electrolytic solution and the counter electrode is in contact with the second electrolytic solution. The solid electrolyte membrane is interposed between the cathode chamber and the anode chamber. The first electrolyte solution contains the carbon dioxide. The working electrode is connected to the counter electrode. An electric source is not interposed electrically between the working electrode and the counter electrode.

A step (b) is a step of irradiating the region with a light having a wavelength of 250 nanometers to 400 nanometers to reduce the carbon dioxide contained in the first electrolyte solution. The working electrode is not irradiated with the light.

The novel method for reducing carbon dioxide according to the present disclosure does not require an electric source interposed between the anode electrode and the cathode electrode.

DESCRIPTION OF EMBODIMENTS

The embodiment of the present disclosure is described below.

Embodiment 1

(Device for Reducing Carbon Dioxide)

Figure 1:
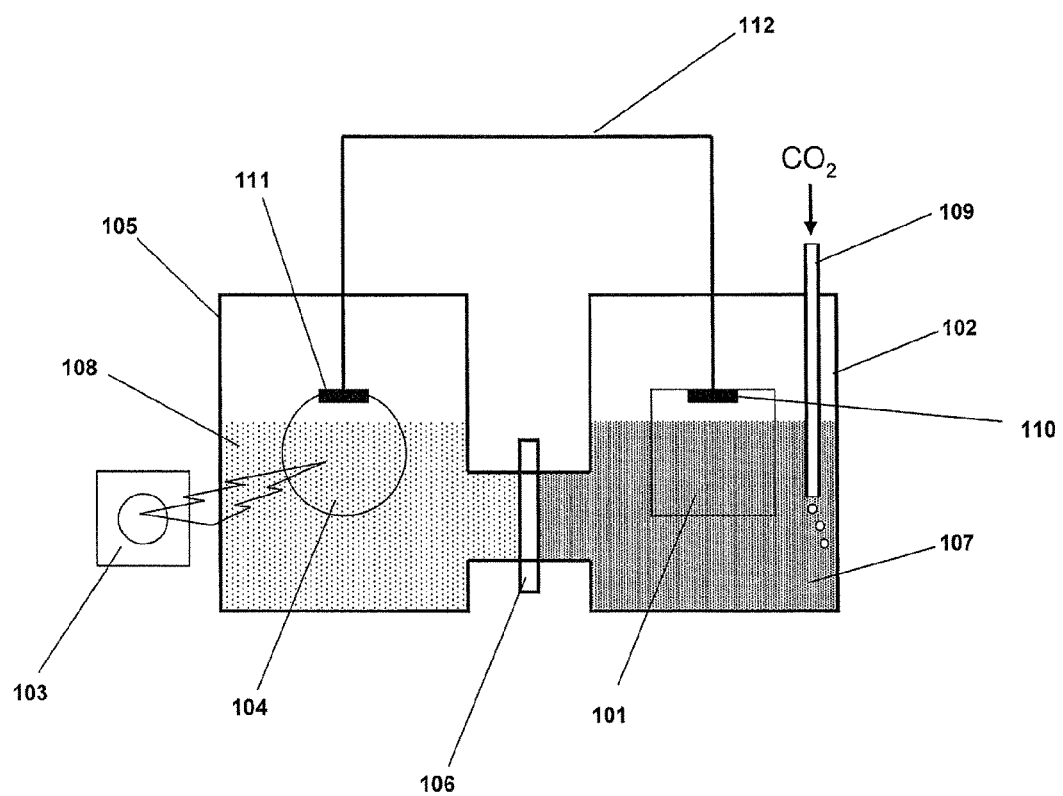
FIG. 1 shows an exemplary schematic view of a device for reducing carbon dioxide according to the embodiment 1.

FIG. 1 shows an exemplary schematic view of a device for reducing carbon dioxide according to the embodiment 1. The device includes a cathode chamber 102, an anode chamber 105, and a solid electrolyte membrane 106.

The cathode chamber 102 includes a working electrode 101.

The working electrode 101 is in contact with a first electrolytic solution 107. Particularly, the working electrode 101 is immersed in the first electrolytic solution 107.

An example of the material of the working electrode 101 is copper, gold, silver, cadmium, indium, tin, lead, or alloy thereof. Copper is preferred. In order to increase an amount of formic acid, indium is preferred. Another example of the material of the working electrode 101 is a metal compound capable of reducing carbon dioxide. Only a part of the working electrode 101 may be immersed in the first electrolytic solution 107, as long as the material is in contact with the first electrolytic solution 107.

The anode chamber 105 includes a counter electrode 104.

The counter electrode 104 is in contact with a second electrolytic solution 108. Particularly, the counter electrode 104 is immersed in the second electrolytic solution 108.

Figure 2A:
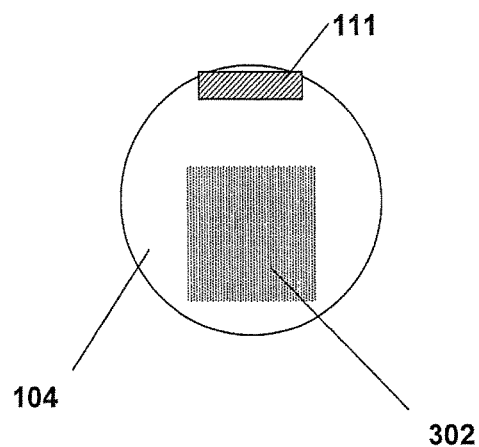
FIG. 2A shows an exemplary schematic view of a counter electrode 104 where a metal wire 303 is not formed.

As shown in FIG. 2A, the counter electrode 104 includes a nitride semiconductor region 302 formed of nitride semiconductor on the surface thereof. It is preferred that the nitride semiconductor is gallium nitride or aluminum gallium nitride. In FIG. 2A, the square nitride semiconductor region 302 is formed on a part of the surface of the counter electrode 104. However, the nitride semiconductor region 302 may be formed on the whole surface of the counter electrode 104. The shape of the nitride semiconductor region 302 is not limited to a square.

Figure 2B:
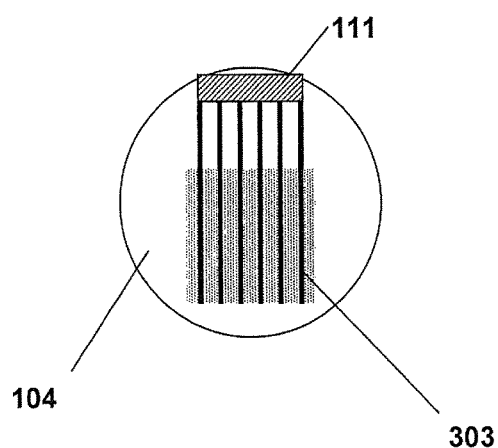
FIG. 2B shows an exemplary schematic view of a counter electrode 104 where a plurality of linear metal wires 303 are formed.
Figure 2C:
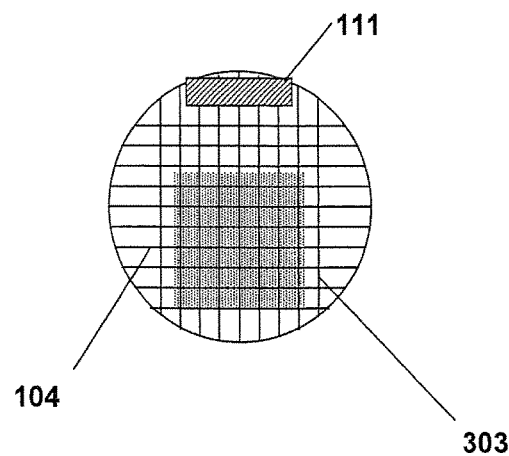
FIG. 2C shows an exemplary schematic view of a counter electrode 104 where a plurality of linear metal wires 303 with a shape of a mesh are formed.

As shown in FIG. 2B and FIG. 2C, it is preferable that a metal wire 303 is provided on the nitride semiconductor region 302. It is preferred that the metal wire 303 is in contact with the nitride semiconductor region 302. As described later, the nitride semiconductor region 302 is irradiated with a light from a light source 103. The metal wire 303 is also irradiated with the light.

As shown in FIG. 2B, a plurality of metal wires 303 may be provided. Each metal wire has a line shape. The plurality of metal wires 303 are arranged in parallel to one another.

As shown in FIG. 2C, a plurality of metal wires 303 having a shape of a mesh may be provided. The shape of the metal wire(s) is not limited.

It is preferable that the metal wire 303 forms an ohmic contact with the nitride semiconductor. An example of the suitable material of the metal wire 303 is titanium. Particularly, the metal wire 303 is a titanium wire, a titanium/nickel stacked wire, a titanium/aluminum stacked wire, a titanium/gold stacked wire, or a titanium/silver stacked wire. A titanium/nickel stacked wire is preferred.

Only a part of the counter electrode 104 may be immersed in the second electrolytic solution 108 as long as the nitride semiconductor is in contact with the second electrolytic solution 108.

The first electrolytic solution 107 is held in the cathode chamber 102. The second electrolytic solution 108 is held in the anode chamber 105.

An example of the first electrolytic solution 107 is a potassium bicarbonate aqueous solution, a sodium bicarbonate aqueous solution, a potassium chloride aqueous solution, a potassium sulfate aqueous solution, or a potassium phosphate aqueous solution. A potassium bicarbonate aqueous solution is preferred. Preferably, the first electric solution 107 is mildly acidic in the condition where carbon dioxide is dissolved in the first electric solution 107.

An example of the second electrolytic solution 108 is a sodium hydroxide aqueous solution or a potassium hydroxide aqueous solution. A sodium hydroxide aqueous solution is preferred. Preferably, the second electrolytic solution 108 is strongly basic.

The solute of the first electrolytic solution 107 may be identical to that of the second electrolytic solution 108; however, it is preferable that the solute of the first electrolytic solution 107 is difficult from that of the second electrolytic solution 108.

The first electrolytic solution 107 contains carbon dioxide. The concentration of the carbon dioxide is not limited.

In order to separate the first electrolytic solution 107 from the second electrolytic solution 108, the solid electrolyte membrane 106 is interposed between the cathode chamber 102 and the anode chamber 105. Namely, the first electrolytic solution 107 and the second electrolytic solution 108 are not mixed in the present device.

A material for the solid electrolyte membrane 106 is not limited, as long as only a proton penetrates the solid electrolyte membrane 106 and other materials can not penetrate the solid electrolyte membrane 106. An example of the solid electrolyte membrane 106 is Nafion (Registered Trade Mark).

The working electrode 101 includes a working electrode terminal 110. The counter electrode 104 includes a counter electrode terminal 111. The working electrode terminal 110 and the counter electrode terminal 111 are electrically connected through a conductive wire 112. Namely, the working electrode 101 is electrically connected to the counter electrode 104 through the conductive wire 112. As shown in FIG. 2B and FIG. 2C, the metal wire 303 is electrically connected to the counter electrode terminal 111. Unlike Patent Literatures 1-2, an electric source is not interposed electrically between the working electrode 101 and the counter electrode 104 in the present disclosure. An example of the electric source is a battery and a potentiostat.

(Method for Reducing Carbon Dioxide)

Next, the method for reducing carbon oxide with the use of the above-mentioned device is described below.

The device is put at a room temperature and under atmospheric pressure.

As shown in FIG. 1, a nitride semiconductor region 302 is irradiated with the light from the light source 103. At least part of the nitride semiconductor region 302 is irradiated with the light. The whole nitride semiconductor region 302 may be irradiated with the light.

An example of the light source 103 is a xenon lamp.

The working electrode 101 is not irradiated with the light.

It is preferred that the light from the light source 103 have a wavelength of not less than 250 nanometers and not more than 400 nanometers. Preferably, the light has a wavelength of not less than 250 nanometers and not more than 365 nanometers.

The metal wire 303 may be provided on the obverse surface of the nitride semiconductor region 302. Namely, the metal wire 303 and the nitride semiconductor region 302 are irradiated with the light from the light source 103. Furthermore, it is preferable that the metal wire 303 is covered with an insulating material (not shown).

As shown in FIG. 1, the device preferably includes a tube 109. It is preferred that the carbon dioxide contained in the first electrolytic solution 107 is reduced while carbon dioxide is supplied through the tube 109 to the first electrolytic solution 107. One end of the tube 109 is immersed in the first electrolytic solution 107. It is preferred that a sufficient amount of carbon dioxide is dissolved in the first electrolytic solution 107 by supplying carbon dioxide through the tube 109 before the reduction of carbon dioxide starts.

The carbon dioxide contained in the first electrolytic solution 107 is reduced to form carbon monoxide or formic acid, when the working electrode 101 includes metal such as copper, gold, silver cadmium, indium, tin, or lead.

EXAMPLES

The present subject matter is described in more detail with reference to the following example.

Example 1

(Preparation of the Counter Electrode)

An n-type gallium nitride film was epitaxially grown on a sapphire substrate by a metal organic chemical vapor deposition method. The n-type gallium nitride film corresponds to the nitride semiconductor region 302. Next, metal wires 303 having a shape of a mesh were formed with an ordinary semiconductor process such as a photolithography, an electron beam deposition, and a lift off technique. The metal wires 303 were made of a Ti/Ni bilayer. The metal wires 303 had a width of 20 micrometers and a thickness of 0.5 micrometers. The interval between two adjacent wires in the mesh was 50 micrometers. A counter electrode terminal 111 which was electrically connected to the metal wires 303 was formed. Thus, as shown in FIG. 2C, obtained was the counter electrode 104 including a nitride semiconductor region 302 formed of the n-type gallium nitride including the metal wires 303.

(Assemblage of the Device)

The device for reducing carbon dioxide shown in FIG. 1 was formed with the use of the counter electrode 104. The device is described below in more detail.

Working electrode 101: A Copper plate

First electrolytic solution 107: Aqueous potassium bicarbonate with a concentration of 0.1 mol/L (180 ml)

Second electrolytic solution 108: Aqueous sodium hydroxide with a concentration of 1.0 mol/L (180 ml)

Solid electrolyte membrane 106: Nafion membrane (available from DuPont Kabushiki Kaisha, trade name: Nafion 117)

Light source 103: Xenon Lamp (Output: 300 W)

The light source 103 emitted a broad light with a wavelength of 250 nanometers to 400 nanometers.

(Reduction of Carbon Dioxide)

Carbon dioxide was supplied for thirty minutes through the tube 109 to the first electrolytic solution 107 by bubbling.

The anode chamber 105 had a window (not shown). The nitride semiconductor region 302 was irradiated with the light from the light source 103 through the window.

Figure 3:
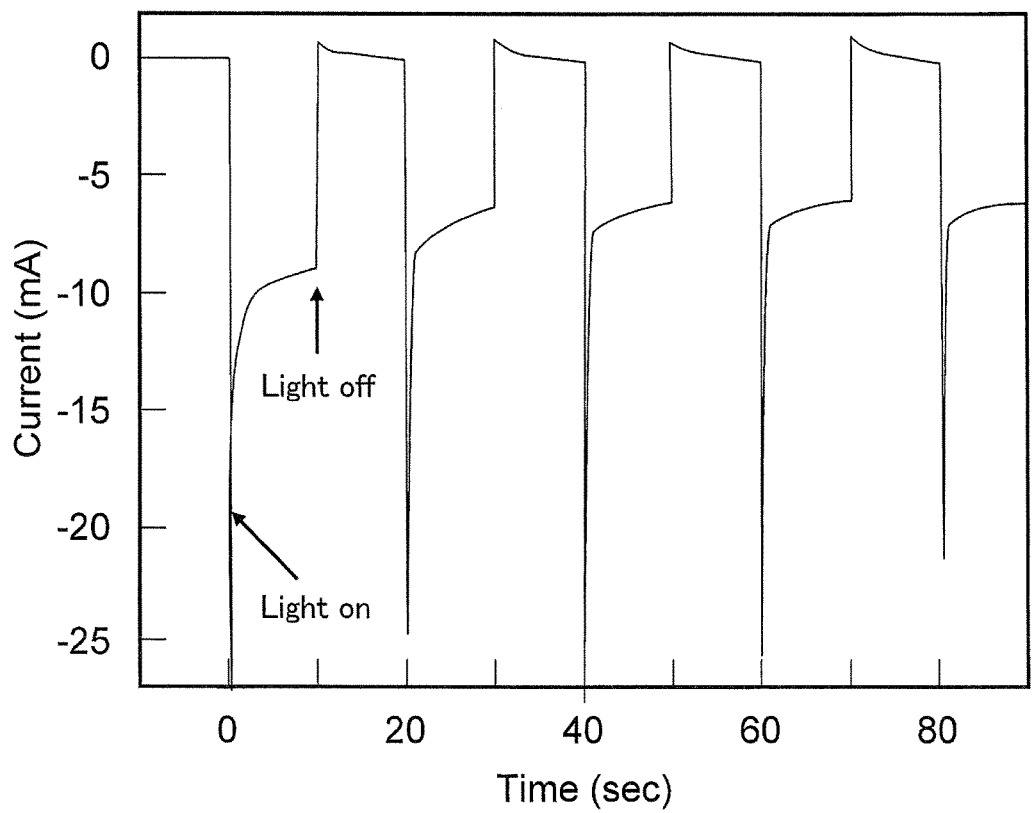
FIG. 3 is a graph showing a current change before and after the nitride semiconductor region 302 was irradiated with the light in example 1.

FIG. 3 is a graph showing a current change before and after the nitride semiconductor region 302 was irradiated with the light. As shown in FIG. 3, when the nitride semiconductor region 302 was irradiated with the light, a current flew through the wire 112. When the region was not irradiated with the light, the flow of the current stopped. This means that a reaction was occurred in at least one electrode of the working electrode 101 and the counter electrode 104.

The present inventors investigated the reaction in more detail as below. Particularly, after the cathode chamber 102 was sealed, the nitride semiconductor region 302 was irradiated with the light once again. A gas component generated in the cathode chamber 102 was analyzed with a gas chromatography. A liquid component generated in the cathode chamber 102 was analyzed with a liquid chromatography.

As a result, it was confirmed that formic acid, carbon monoxide, and methane were generated in the cathode chamber 102.

Figure 4:
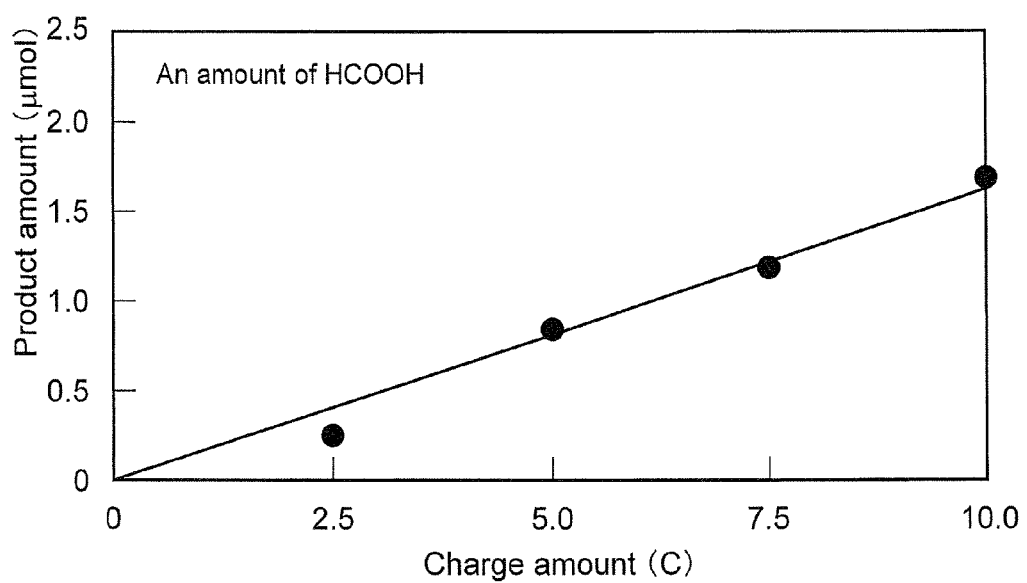
FIG. 4 shows a relationship between the charge amount (horizontal axis) and the amount of the formic acid (vertical axis) in example 1.

Furthermore, a charge amount (coulomb amount) relevant to the reaction was calculated from the light current amount caused by the irradiation of the light. FIG. 4 shows a relationship between the charge amount (horizontal axis) and the amount of the formic acid (vertical axis). As is clear from FIG. 4, the amount of the formic acid was proportional to the charge amount. This means that a catalytic reaction where the carbon dioxide was reduced was occurred due to the irradiation of the light.

Example 2

An identical experiment to example 1 was performed except that metal wires 303 made of nickel were used instead of the metal wires 303 made of the Ti/Ni bilayer.

Example 3

As shown in FIG. 2A, an identical experiment to example 1 was performed except that metal wires 303 were not formed.

Figure 5:
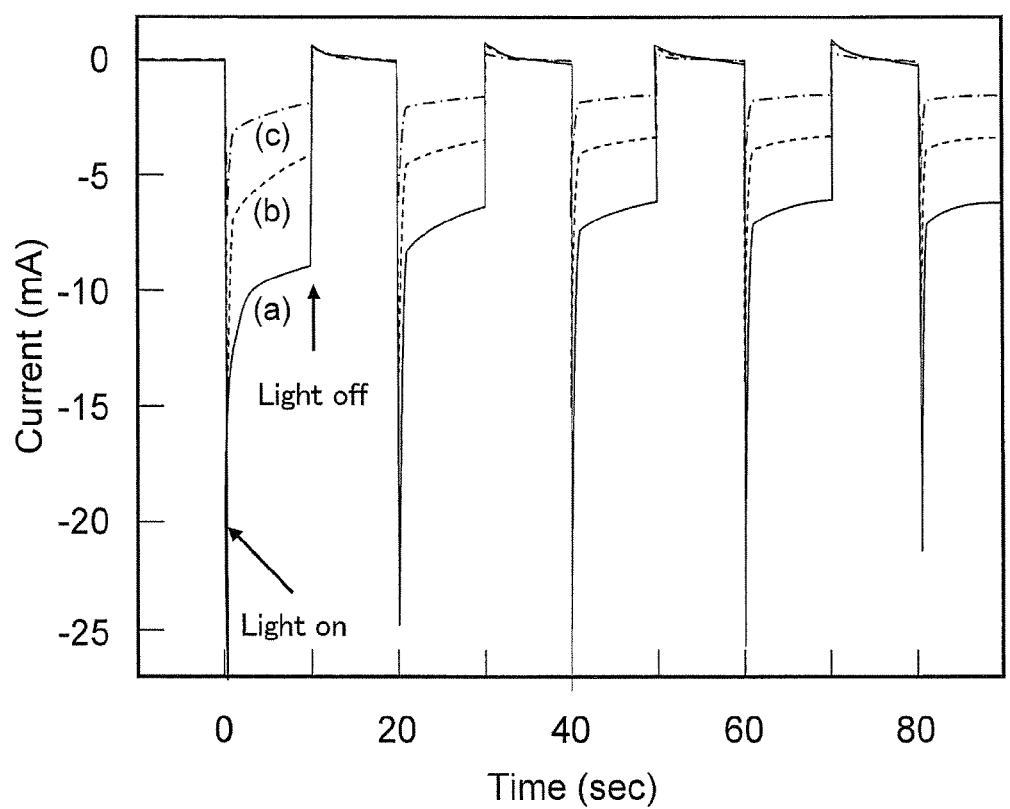
FIG. 5 is a graph showing a current change before and after the nitride semiconductor region 302 was irradiated with the light in example 1, example 2, and example 3.

FIG. 5 is a graph showing a current change before and after the nitride semiconductor region 302 was irradiated with the light in example 1, example 2, and example 3. In FIG. 5, the referential signs (a), (b), and (c) indicate the results of example 1, example 2, and example 3, respectively. As shown in FIG. 5, the current amount in example 1 was the largest, and the current amount in example 3 was the smallest.

Figure 6:
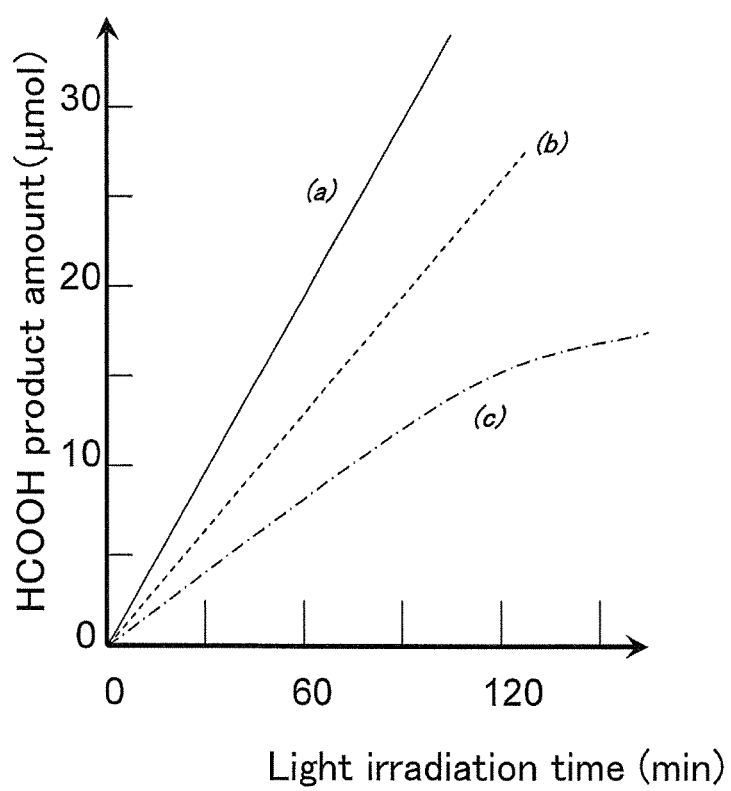
FIG. 6 is a graph showing the period of the irradiation of the light (horizontal axis) and the product amount of the formic acid (vertical axis) in examples 1-3.

FIG. 6 shows the period of the irradiation of the light (horizontal axis) and the product amount of the formic acid (vertical axis). In FIG. 6, the referential signs (a), (b), and (c) indicate the results of example 1, example 2, and example 3, respectively. As shown in FIG. 6, when the periods of the irradiation of the light are identical, the amount of the formic acid produced in example 1 was the largest, and the amount of the formic acid produced in example 3 was the smallest.

As is clear from FIG. 5 and FIG. 6, the production amount per unit time of the formic acid was increased when the metal wires 303 were used. The production amount per unit time of the formic acid was more increased when the metal wires 303 made of the Ti/Ni bilayer was used.

INDUSTRIAL APPLICABILITY

The present subject matter provides a method for reducing carbon dioxide.

REFERENCE SIGNS LIST

101: working electrode
102: cathode chamber
104: counter electrode
105: anode chamber
106: solid electrolyte membrane
107: first electrolyte solution
108: second electrolyte solution
302: region
303: metal wire

What is claimed is:

1. A method for reducing carbon dioxide with use of a device for reducing carbon dioxide, the method comprising:
a step (a) of preparing the device for reducing carbon dioxide, the device comprising:
a cathode chamber;
an anode chamber; and
a solid electrolyte membrane; wherein:
the cathode chamber comprises a working electrode,
the working electrode comprises a metal or a metal compound,
the anode chamber comprises a counter electrode,
the counter electrode comprises a region formed of a nitride semiconductor on the surface thereof,
a first electrolytic solution is held in the cathode chamber,
a second electrolytic solution is held in the anode chamber,
the working electrode is in contact with the first electrolytic solution,
the counter electrode is in contact with the second electrolytic solution,
the solid electrolyte membrane is interposed between the cathode chamber and the anode chamber,
the first electrolyte solution contains the carbon dioxide,
the working electrode is connected to the counter electrode, and
an electric source is not interposed electrically between the working electrode and the counter electrode;

a step (b) of irradiating the region with a light having a wavelength of 250 nanometers to 400 nanometers to reduce the carbon dioxide contained in the first electrolyte solution, wherein the working electrode is not irradiated with the light.

2. The method according to claim 1, wherein the nitride semiconductor is gallium nitride.

3. The method according to claim 2, wherein the nitride semiconductor is n-type.

4. The method according to claim 1, wherein the nitride semiconductor is aluminum gallium nitride.

5. The method according to claim 4, wherein the nitride semiconductor is n-type.

6. The method according to claim 1, wherein the working electrode comprises a metal.

7. The method according to claim 6, wherein the metal is copper, gold, silver, cadmium, indium, tin, lead or alloy thereof.

8. The method according to claim 7, wherein the metal is copper.

9. The method according to claim 7, wherein the metal is indium.

10. The method according to claim 8, wherein the first electrolyte solution is a potassium bicarbonate aqueous solution.

11. The method according to claim 1, wherein the first electrolyte solution is a potassium bicarbonate aqueous solution, a sodium bicarbonate aqueous solution, a potassium chloride aqueous solution, a potassium sulfate aqueous solution, or a potassium phosphate aqueous solution.

12. The method according to claim 1, wherein the second electrolyte solution is a sodium hydroxide aqueous solution or a potassium hydroxide aqueous solution.

13. The method according to claim 1, wherein in the step (b), the device is left at a room temperature and under atmospheric pressure.

14. The method according to claim 1, wherein:
a metal wire is provided on the surface of the region, and
not only the region but also the metal wire are irradiated with the light.

15. The method according to claim 14, wherein:
a plurality of the metal wires is provided, and
each of the metal wires is parallel to one another.

16. The method according to claim 14, wherein:
a plurality of the metal wires is provided, and
the plurality of metal wires have a shape of a mesh.

17. The method according to claim 14, wherein the metal wire comprises titanium.

18. The method according to claim 14, wherein the metal wire comprises nickel.

19. The method according to claim 14, wherein the metal wire comprises titanium/nickel stacked wire.

20. The method according to claim 1, wherein in the step (b), at least formic acid is obtained.

21. The method according to claim 1, wherein in the step (b), at least carbon monoxide is obtained.

22. The method according to claim 1, wherein in the step (b), at least methane is obtained.

23. The method according to claim 1, wherein in the step (b), at least one of formic acid, carbon monoxide and methane is obtained.

* * * * *